(12) United States Patent
Reddy

(10) Patent No.: US 8,129,147 B2
(45) Date of Patent: Mar. 6, 2012

(54) MENINGOCOCCAL OLIGOSACCHARIDE LINKED POLYSACCHARIDES AND DIPTHERIA PROTEIN CONJUGATE VACCINE FOR ALL AGES

(75) Inventor: Jeeri R Reddy, Omaha, NE (US)

(73) Assignee: Jeeri R. Reddy, Omaha, NE (US)

( * ) Notice: Subject to any disclaimer, the term of this patent is extended or adjusted under 35 U.S.C. 154(b) by 40 days.

(21) Appl. No.: 12/834,532

(22) Filed: Jul. 12, 2010

(65) Prior Publication Data

US 2010/0297166 A1 Nov. 25, 2010

Related U.S. Application Data

(63) Continuation-in-part of application No. 11/680,471, filed on Feb. 28, 2007, now Pat. No. 7,491,517.

(60) Provisional application No. 60/831,682, filed on Jul. 19, 2006.

(51) Int. Cl.
*C12P 19/00* (2006.01)
*C12P 19/26* (2006.01)
*C12N 1/12* (2006.01)
*C12N 1/20* (2006.01)
*A61K 39/095* (2006.01)

(52) U.S. Cl. ......... 435/72; 435/84; 435/101; 435/252.1; 435/253.6; 424/250.1

(58) Field of Classification Search .......... None
See application file for complete search history.

(56) References Cited

U.S. PATENT DOCUMENTS 4,695,624 A * 9/1987 Marburg et al. ......... 424/197.11
2005/0089968 A1 * 4/2005 Olivieri et al. ............... 435/69.3

OTHER PUBLICATIONS

Fu et al. (Biotechnology 13:170-174, 1995).*
Atlas, Ronald (Handbook of Microbiological Media, 2nd edition 1997, p. 1368).*

* cited by examiner

*Primary Examiner* — Oluwatosin Ogunbiyi

(57) ABSTRACT

Methods for producing quadrivalent meningococcal meningitis polysaccharide and conjugate vaccines for serotypes A, C, Y and W-135 disclosed. *Neisseria meningitidis* fastidious medium was designed to maximize the yield of capsular polysaccharides and generate minimal cellular biomass and endotoxin in a short duration of fermentation. The crude polysaccharides are isolated, purified, and mechanically depolymerized by sonication. These purified polysaccharides were found in human clinical trials to be safe and immunogenic against meningococcal disease caused by *N. meningitidis* A, C, Y and W-135 serogroups in sub-Saharan Africa. In the preferred embodiment, the polysaccharides are conjugated to carrier proteins of diphtheria or tetanus toxoid to an average molecular size of 5100 to 9900 Daltons and provide broad spectrum protection to humans of all ages. Accelerated polysaccharide production and the efficacy of the resulting vaccine are demonstrated.

2 Claims, 4 Drawing Sheets

Fig. 1. Neisseria meningitidis serogroup A Polysaccharides (PS) production in NMFM Media versus bacterial growth in 250 liter Fermentor with 100-liters working volume Fig. 2. Neisseria meningitidis serogroup C Polysaccharides (PS) production in NMFM Media versus bacterial growth in 250 liter Fermentor with 100-liters working volume Fig. 3. Neisseria meningitidis serogroup Y Polysaccharides (PS) production in NMFM Media versus bacterial growth in 250 liter Fermentor with 100-liters working volume Fig. 4. Neisseria meningitides serogroup W-135 Polysaccharides (PS) production in NMFM Media versus bacterial growth in 250 liter Fermentor with 100-liters working volume

US 8,129,147 B2

MENINGOCOCCAL OLIGOSACCHARIDE LINKED POLYSACCHARIDES AND DIPTHERIA PROTEIN CONJUGATE VACCINE FOR ALL AGES

CROSS-REFERENCE TO RELATED APPLICATIONS

This application is a continuation-in-part application of U.S. Ser. No. 11/680,471, filed Feb. 28, 2007, now based on the U.S. Pat. No. 7,491,517 which was filed as a provisional application U.S. Ser. No. 60/831,682 filed on Jul. 19, 2006.

BACKGROUND OF THE INVENTION

1. Field of the Invention

The present invention generally relates to the field of medical microbiology and immunology. In particular, the invention pertains to an improved vaccine for immunization.

2. Description of the Related Art

Neisseria meningitidis (the meningococcus), identified in 1887 is one of the causative agents of meningococcal meningitis. Twelve subtypes or serogroups of N. meningitidis have been identified and four (N. meningitidis. A, B, C and W-135) are known to cause epidemics. The most common symptoms are stiff neck, high fever, sensitivity to light, confusion, headaches, and vomiting. Even when the disease is diagnosed early and adequate therapy instituted, 5% to 10% of patients die, typically within 24-48 hours of the onset of symptoms. The 10 to 20% of the survivors suffer brain damage, hearing loss, or learning disability. A less common but more severe (often fatal) form of meningococcal disease is meningococcal septicaemia which is characterized by a haemorrhagic rash and rapid circulatory collapse.

Meningococcal bacteria incorporate polysaccharides into their surface structure. Thus a large majority of bacteria are covered with of capsule or glyco-calyx polysaccharide which induces an immunological response in humans. The outer membrane of gram-negative Neisseria meningitidis (NM) bacterium consists, inter alia, of lipopolysaccharide (LPS). Such polysaccharides (PS) are formed on the basis of repeating units in which the constituents and the bonds are defined and which are each characteristics of the NM serogroups defined. These repeating units contain the epitopes which are the antigenicity-determining structures.

The immunogenicity of the capsular polysaccharides to carrier protein can be improved by coupling them to Lipo-oligosaccharides (LOS). When covalently linked to a carrier protein, the resulting PS component in a conjugate vaccine becomes a T cell-dependent (TD) antigen inducing long-term immunity with immune memory even in infants and young children. Further, additional linkage with oligosaccharide (OS) makes a robust conjugate vaccine since OS not only acts as additional immunogen but also as a vaccine adjuvant.

EXISTING STATE OF THE ART

The existing state of art has many problems as discussed. Precipitating polysaccharides with phenolic extraction for removing components (impurities) like lipopolysaccharide endotoxin results in phenolic contaminants interfering with the pure polysaccharide production process. Similarly, precipitating with catalyon and depolymerised chemical hydrolysis also have problems like depolymerization interfering with purity in vaccine production.

Existing art for depolymerization of polysaccharide by chemical means and conjugation of polysaccharides with carrier proteins activated by chemical means state that the chemical residues tend to induce adverse side effects during routine immunization or the average size of the polysaccharides obtained may not provide efficient immune response in humans. Similarly, existing art regarding the inclusion of adjuvant for enhancing immunogenicity against the different serotypes of N. meningitidis may have adverse side effects during routine immunization.

Large scale biomass production with reduced production of capsular polysaccharides is found in the prior art. Existing art on animal free meningococcal polysaccharide fermentation medium with soy peptone as nitrogen source requires pH adjustment during fermentation. Also the high glucose utilization in the medium results in excessive cellular biomass.

The current vaccines against this pathogen (Neisseria meningitidis) have the following disadvantage such as the serogroups A, C, Y, and W-135 capsular plain polysaccharide and the capsular polysaccharide diphtheria conjugate vaccine are not for all ages and less immunogenic in young children, especially infants.

Therefore there is a need for an invention to eliminate the short-comings in the prior art and to invent a method of producing a meningococcal meningitis vaccine without any chemical impurities or residues (to eliminate the disadvantages regarding depolymerization and conjugation by chemical means and capsular polysaccharide size) and a medium for producing it, which ensures higher yield of polysaccharides and lower yield of cellular biomass to facilitate the production and purification processes of vaccine production. Also there is a need for an improved meningococcal vaccine to prevent meningitis deaths in toddlers and be a vaccine for all ages. Therefore it is an object of the present invention to invent a method of producing meningococcal meningitis vaccine comprising N. meningitidis serotypes A, C, Y and W-135 having long lasting effect and provide broad spectrum immunity to humans of all age groups.

It is yet another object of the present invention to develop a method wherein trace chemical impurities currently present in the available meningococcal meningitis vaccine are eliminated by a mechanical method, preferably sonication.

Another object of the present invention is to invent a composition of a medium that yields a higher percentage of polysaccharides in comparison to known media employed for producing meningococcal meningitis vaccine.

It is yet another object of the present invention to invent a composition of a medium that yields a lower percentage of cellular biomass in comparison with known media employed for producing meningococcal meningitis vaccine.

It is yet another object of the invention to identify an optimum molecular size of N. meningitidis polysaccharides of serogroups A, C, Y and W-135 that confers broad spectrum immunogenic protection against meningitis.

It is yet another object of the present invention to invent an improved capsular polysaccharide diphtheria conjugate vaccine for meningococcal meningitidis that prevent meningitidis deaths even in toddlers and be a vaccine for all ages.

Another object of the present invention is to develop a process for the production of an improved capsular polysaccharide diphtheria conjugate vaccine and its use especially as vaccinal agent.

The invention which was the subject matter of U.S. Pat. No. 7,491,517 was invented by this applicant and was well received and patented. However the need to reduce the costs in the medium preparation remains a continuous one as this can bring down the costs of the vaccine making it accessible to greater number of people.

BRIEF SUMMARY OF THE INVENTION

Methods for producing a quadrivalent polysaccharide vaccine of serotypes A, C, Y and W-135 for meningococcal meningitidis by mechanical means: The methods employ modified *Neisseria meningitidis* fastidious medium specially formulated to be more economical and cheaper than the previous NMFM medium but with the same yield of capsular polysaccharides, cellular biomass and endotoxins. The crude polysaccharides are isolated and purified by ultra-filtration and gently treated with a polycationic compound that precipitates the polyanionic capsular polysaccharides to maximize the yield of precipitated polysaccharides from liquid cultures. The polysaccharides are then mechanically depolymerized, preferably by sonication. The pure polysaccharides were found in human clinical trials to be highly effective against meningitis caused by *N. meningitidis* A, C, Y and W-135 serogroups. In the most preferred embodiment the pure polysaccharides are conjugated to carrier proteins of diphtheria or tetanus toxoid to provide broad spectrum protection to humans of all age groups.

The present invention is directed to a method of preparing modified NMFM medium comprising sodium chloride (NaCl), potassium phosphate dibasic (K2HPO4), ammonium chloride (NH4Cl), potassium sulphate (K2SO4), magnesium chloride ((MgCl2.6H2O), calcium chloride (CaCl2.2H2O), glucose, L-glutamic Acid, L-arginine, glycine, L-serine, L-cysteine.HCl, Fe (III) citrate, yeast extract (30 k dia-filtered) and antifoam dissolved in DI water. The specific formulation used in the experiments conducted is given below.

Composition of Modified *Neisseria meningitidis* Fastidious Medium (NMFM) for Serogroups A, C, Y and W-135: (Grams Per Liter)

| Component | g/L or mL/L |
|---|---|
| DI Water (initial) | 800 mL |
| Sodium Chloride (NaCl) | 5.60 |
| Potassium Phosphate Dibasic (K2HPO4) | 4.10 |
| Ammonium Chloride (NH4Cl) | 1.00 |
| Potassium Sulphate (K2SO4) | 0.90 |
| Magnesium Chloride ((MgCl2•6H2O) | 0.35 |
| Calcium Chloride (CaCl2•2H2O) | 0.03 |
| Glucose | 10.00 |
| L-Glutamic Acid | 3.80 |
| L-Arginine | 0.10 |
| Glycine | 0.20 |
| L-Serine | 0.50 |
| L-Cysteine•HCl | 0.10 |
| Fe (III) Citrate | 0.04 |
| Yeast Extract (30k dia-filtered) | 0.1% |
| Antifoam | 0.1 mL |

Filter sterilized glucose and amino acids were added to the autoclaved cool medium, which improved production of polysaccharides by 25%. This process allows non-degradation of heat sensitive sugars and amino acids and eliminates batch feeding during the fermentation process for polysaccharide production. The above modified medium is specially formulated to make the medium more economical and cheaper than the previous NMFM medium and to produce results similar to previous NMFM media like increase in the production of capsular polysaccharide and decrease in the production of cellular biomass. One more special feature of the medium is that the pH is maintained from about 6.5 to 7.0 during the fermentation process without using buffers and pH probes. Here in this invention the phenol extraction step of the purification process found in the prior art is replaced by activated carbon filtration to avoid any phenol interaction during purification. The isolated polyanionic polysaccharides are then precipitated with a polycationic compound. The precipitated polysaccharides are then subjected to ultra-filtration for the isolation of pure polysaccharides. The isolated pure polysaccharides are depolymerized by sonication. These low molecular weight polysaccharides proved very effective when compared with other inventions. The human trials for pure polysaccharides of serotypes A, C, Y and W-135 of this invention indicated very mild adverse side effects, none of which were severe, and also proved to be very effective for humans above the age of 13 years and may provide effective protection against meningococcal meningitis for humans above the age of 5 years.

In another preferred embodiment the pure low molecular weight polysaccharides were conjugated to carrier proteins of diphtheria toxoids to produce quadrivalent meningococcal meningitis conjugated vaccine for the serotypes A, C, Y and W-135. This conjugated vaccine proved effective for all ages. The vaccine proved to be non-toxic and immunogenic in animal trials using neonatal mice and mice of 7-8 weeks. The use of mice models in animal trials show that the conjugated quadrivalent polysaccharide vaccine A, C, Y and W-135 may also be effective in risk age groups (children below 2 years) and can immunize effectively humans of all ages.

The present invention is directed to a method of deriving an oligosaccharide from *Neisseria meningitidis* (NM) serogroups A, C, Y and W-135 and linking it between antigenic activated *Neisseria meningitidis* serogroups A, C, Y and W-135 polysaccharide and diphtheria toxoid, a process for preparing it and its use especially as vaccinal agent.

BRIEF DESCRIPTION OF SEVERAL VIEWS OF DRAWINGS

FIG. 1 *Neisseria meningitidis* serogroup A Polysaccharides (PS) production in NMFM Media versus bacterial growth in 250 liter Fermentor with 100-liters working volume.

FIG. 2 *Neisseria meningitidis* serogroup C Polysaccharides (PS) production in NMFM Media versus bacterial growth in 250 liter Fermentor with 100-liters working volume.

FIG. 3 *Neisseria meningitidis* serogroup Y Polysaccharides (PS) production in NMFM Media versus bacterial growth in 250 liter Fermentor with 100-liters working volume.

FIG. 4 *Neisseria meningitides* serogroup W-135 Polysaccharides (PS) production in NMFM Media versus bacterial growth in 250 liter Fermentor with 100-liters working volume.

DEFINITION

Modified NMFM indicates Modified *Neisseria meningitidis* Fastidious Medium.

DETAILED DESCRIPTION OF THE INVENTION

*N. meningitidis* serogroup A, C, Y and W-135 Polysaccharides comprise the vaccine against meningitis. The goal of this experiment was to compare our invented medium with two commonly used cultivation media for production of polysaccharides. Our NM Fastidious Medium (NMFM) was compared with Watson-Scherp and Catlin Media. The comparative criteria was based on the final polysaccharide concentrations and the yield coefficient cell/polysaccharide ($Y_{P/X}$). The kinetic parameters: pH, substrate consumption and cell growth. Cultivation of meningococcal serotypes was carried out in a 100 L New Brunswick® bioreactor, under the following conditions: 80 L of culture medium, temperature 35.degree. C., 6% $CO_2$, air flow 5 L/min, agitation frequency 120 rpm and vessel pressure 6 psi, without dissolved oxygen or pH controls. The cultivation runs were divided in three groups, with 3 repetitions each. The cultivations using NM Fastidious Medium (NMFM) presented the best results: average of four serotypes final polysaccharide concentration at 12 hours in 80 Liters=45.25 mg/L and $Y_{P/X}$=0.13, followed by Watson-Scherp medium with results of 27.00 mg/L and $Y_{P/X}$=0.07 and Catlin medium results of 22.5 mg/L and $Y_{P/X}$=0.05 a respectively. The principal advantage we claim here is in the use of the NMFM for better vaccine production or polysaccharide yield than Watson-Scherp and Catlin media.

DETAILED DESCRIPTION OF THE PREFERRED EMBODIMENT

Several synthetic media were discovered for large-scale production of meningococcal meningitidis polysaccharide. Polysaccharide production in batch process of *Neisseria meningitidis* serogroup C comparing Frantz, modified Frantz and Catlin 6 cultivation media. None of these media eliminated the problems associated with longer duration of fermentation and limitations on endotoxin production. Greatest emphasis was placed on the cost of media components, not on the time associated with fermentation or with the expenses for endotoxin removal or with the time associated with the production of meningococcal polysaccharide vaccine. Though NMFM medium is more expensive than other synthetic media, large-scale production of meningococcal meningitidis polysaccharide using NMFM medium eliminates the longer fermentation process. A major advantage of NMFM medium is the elimination of endotoxin in the polysaccharide purification process for a given time.

The main aim of this invention is to make the medium more economical and cheaper thereby cutting down the cost of the vaccine, making it available to the public at reasonably affordable prices.

The detailed method of preparation of modified NMFM in various culture volumes is described in the following paragraphs:

Composition of Modified *Neisseria meningitidis* Fastidious Medium (NMFM) for Serogroups A, C, Y and W-135: (Grams Per Liter)

-continued

| Component | g/L or mL/L |
|---|---|
| DI Water (initial) | 800 mL |
| Sodium Chloride (NaCl) | 5.60 |
| Potassium Phosphate Dibasic (K2HPO4) | 4.10 |
| Ammonium Chloride (NH4Cl) | 1.00 |
| Potassium Sulphate (K2SO4) | 0.90 |
| Magnesium Chloride ((MgCl2•6H2O) | 0.35 |
| Calcium Chloride (CaCl2•2H2O) | 0.03 |
| Glucose | 10.00 |
| L-Glutamic Acid | 3.80 |
| L-Arginine | 0.10 |
| Glycine | 0.20 |
| L-Serine | 0.50 |
| L-Cysteine•HCl | 0.10 |
| Fe (III) Citrate | 0.04 |
| Yeast Extract (30k dia-filtered) | 0.1% |
| Antifoam | 0.2 mL |

Media Preparation

Modified NMFM Media Preparation for ABI GC5000 250 L Fermentor (130 L)

To prepare medium for the ABI GC 5000 Fermentor (SOP 4020), the mixing tank is filled with an initial volume of DI water and connected to power source. Using a digital balance (SOP 4034) and weighing boats, each component of the modified NMFM media is weighed for preparing the desired volume. Ingredients are added to the mixing tank one by one as per the order listed in the table and each ingredient is allowed to dissolve before the next one is added. Required amount of antifoam is added once the other chemicals have been dissolved. DI water is added to the marked volume on the view glass of the mixing tank (SOP 4039). After all ingredients have been dissolved using the medium tubing and the Masterflex Digital I/P pump (SOP 4022) the medium is transferred into the fermentor. Medium tubing is connected to the bottom valve of the mixing tank using a tri-clamp and the medium is transferred into the fermentor through the media transfer port. The medium should be sterilized after the transfer is complete, (refer to SOP 4020 for sterilization procedure). Glucose solution (SOP 9024) is prepared separately, autoclaved, and added after the remaining medium components are sterilized. In a biological safety cabinet, 33.3 ml 33.3% glucose solution/liter of medium is poured into a large sterile aspirator bottle assembly. The solution is pumped into the fermentor using the Masterflex Digital I/P pump (SOP 4022).

Media Preparation for 30 L Chemap Fermentor (20 L)

To prepare medium for the Chemap Fermentor (SOP 4019), a 4 L beaker is filled with about 3.5 L of DI water and a stir bar is kept inside the beaker. The beaker is placed on a stir plate for stirring (SOP 4006). Using a digital balance and weigh boats, each component of the modified NMFM media is weighed for preparing the desired volume. The actual amount weighed for each ingredient is marked on the modified NMFM medium data form. Ingredients are added to the beaker one by one as per the order listed in the table and each ingredient is allowed to dissolve before the next one is added. Required amount of antifoam is added to the medium and the ingredients are allowed to mix thoroughly until it dissolves. The magnet is removed using a stir bar retriever. 4 L of medium is poured into the Chemap Fermentor using a funnel and the DI water is adjusted to the desired level. The medium is sterilized according to SOP 4019. Glucose solution (SOP 9024) is prepared separately, autoclaved, and added after the remaining medium components are sterilized. In a biological safety cabinet, 33.3 ml 33.3% glucose solution/liter of medium is poured into a small sterile aspirator bottle assembly and the solution is pumped into the fermentor using the Masterflex Digital I/P pump (SOP 4022).

Media Preparation for Neisserial Shake Flask Fermentation:

The medium has four parts of component making.

Part A: Making yeast extract supplement

Part B: Making 5× nutrient mix

Part C: Making 100× Calcium and magnesium salt mix

Part D: Making Glucose supplement

Part A: Making of Yeast Extract Supplement (1% Y.E Supplement):

11 g of yeast extract is weighed and dissolved in 1100 ml of DI water by magnetic stirring. The obtained yeast extract solution is passed through 0.2 µm Nalgene filter. The filtrate is passed through VIVA flow 30K diafiltration unit. The retentate is recycled and the filtrate is collected to remove large molecular weight glucans. Diafiltration is stopped once 1 L filtrate is collected. Residual retentate (about 100 ml) is discarded.

Part B: Making of 5× Nutrient Mix:

| Ingredient | Grams/L |
|---|---|
| Sodium Chloride (NaCl) | 28.0 |
| Potassium Phosphate Dibasic (K2HPO4) | 20.50 |
| Ammonium Chloride (NH4Cl) | 5.00 |
| Potassium Sulphate (K2SO4) | 4.50 |
| L-Glutamic Acid | 19.0 |
| L-Arginine | 0.50 |
| Glycine | 1.0 |
| L-Serine | 2.50 |
| L-Cysteine•HCl | 0.50 |
| Fe(III) Citrate | 0.2 |

The above ingredients are weighed and dissolved in 1 L DI water to constitute 5× nutrient mix.

Part C: Making of 100× Calcium and Magnesium Salt Mix:

| Ingredient | Grams/L |
|---|---|
| Magnesium Chloride ((MgCl2•6H2O) | 35.0 |
| Calcium Chloride (CaCl2•2H2O) | 3.0 |

The above 100× calcium and magnesium salt mix is prepared in DI water and it is filter sterilized using 0.2 micron Nalgene filter.

Part D: Making of Glucose Supplement:

330 grams of glucose supplement is weighed per liter of Di Water (33%) and filter sterilized using 0.2 micron Nalgene filter.

Preparation of 1 L JN NMFM Medium Using Above Four Parts:

200 ml of part B is taken in a clean measuring jar and 100 ml of part A is added to it. The volume is made up to 965 ml with DI water, transferred to an Erlenmeyer flask and autoclaved at 121° C. for 15 minutes. 1 ml of part C and 33.3 ml of part D are added aseptically after the autoclaved medium attains room temperature.

The aim of the study was to describe the dynamic behavior of the bioprocess system of *Neisseria meningitidis* that can be used in future for the control and optimization of the industrial process of capsular polysaccharide production. Inoculation procedure and cultivation conditions were as described later in the document. Samples of cultivation were collected at pre-established time intervals and analytical assays were conducted to obtain the rate of microbial growth, glucose uptake, and polysaccharide production. An analysis of the kinetics of capsular polysaccharide production by *Neisseria meningitidis* serogroups was conducted. Based on microorganism behavior and transient characteristics (common to processes operated in batch operation mode) such as variations in glucose concentration, accumulation of metabolic products and availability of dissolved oxygen, a standard set of bioprocess conditions were developed.

Microbial Growth:

The specific microbial growth rate was directly proportional to the concentration of dissolved oxygen in the cultivation medium. Microbial growth was limited by concentration of glucose and no growth substrate inhibition effects were observed in the glucose concentration studies. Glucose consumption was affected by the availability of dissolved oxygen. During the logarithmic phase, the bacterial growth in the medium showed high oxygen concentration and low glucose uptake, and this was much lower than the highest specific microbial growth rates. Glucose uptake increased when an oxygen concentration of zero was achieved. Thus the rate of glucose (carbohydrate) metabolism by *Neisseria meningitidis* was determined by the availability of oxygen. A buildup of capsular polysaccharide formation occurred because the limited availability of oxygen favored the specific polysaccharide production of serotypes A, C, Y, and W-135. The existence of a maximum quantity of surface polysaccharide for each serotype was observed under the conditions described above.

The process of capsular polysaccharide production by *Neisseria* meningitis serogroups was performed in a 100 Liter bioreactor. Experimental results showed that the availability of dissolved oxygen in the cultivation medium determined kinetics of the *N. meningitidis* bacterium. Higher concentration of oxygen favored microbial growth and decreased the specific capsular polysaccharide production. This could be related to the use of a common lipid intermediate, either in the construction of cell walls, an essential structure for bacterial survival, or in the biosynthesis of capsular polysaccharide. The more rapid accumulation of capsules under low concentration of dissolved oxygen could also be associated with the need to produce this cell protection structure in situations of stress, such as limited availability of oxygen.

The presence of Class 4 proteins of *Neisseria meningitidis* is known to be anti-bactericidal. Therefore we used *Neisseria meningitidis* serogroups A, C, Y and W-135 vaccine strains, which were deleted for Class 4 proteins, in vaccine production by the purification of polysaccharides using novel methodology to produce toxin-free vaccine.

Immunogenicity, pyrogenicity, and toxicity of purified polysaccharides were determined in animals and humans. Immunogenicity of vaccine candidates were tested by ELISA and Serum Bactericidal Assays (SBA) using animal and human sera which showed high serum titers in SBA and high reactivity titers in ELISA in vitro experiments.

Production of Low Molecular Weight Polysaccharides for Meningococcal Meningitis Vaccine—Preparation and Formulation Natural meningococcal meningitidis polysaccharide is about 500,000 to 1,500,000 daltons. A novel extracellular low-molecular-weight polysaccharide was detected within extracellular class 4 deleted mutants of *Neisseria* meningitis serotype cultures.

The present invention is directed towards a non-chemical method (sonication) to make low molecular weight polysaccharides and to produce conjugated meningococcal meningitidis polysaccharides with minimum range of 5100 to 9900 Daltons size.

Compositional analysis, methylation analysis, and nuclear magnetic resonance analysis revealed that this low-molecular-weight polysaccharide was composed of the same polysaccharide repeating unit previously described for the high-molecular-weight form of the polysaccharides synthesized from *Neisseria* meningitis serotypes.

The purified polysaccharides contain high and low molecular weight Extracellular polysaccharides (EPS). Magnetic sonication was done at 4.degree. C. for 2 hours to obtain soluble low molecular weight EPS. The soluble low molecular weight EPS were collected and analyzed by Mass spectrometry which indicated that its size was consistent with a dimeric form of the polysaccharide repeating unit. High-molecular-weight EPS were then removed from concentrated supernatants by centrifugation (12,000.times.g for 10 min). Low-molecular-weight, ethanol-soluble polysaccharides were then purified from concentrated supernatants using gel permeation chromatography.

EXAMPLE

Fermentation Procedure

The working Seed Bank stocks of *Neisseria meningitidis* A, C, Y, W-135 were kept frozen in glycerol solution at −80.degree. C. These stock tubes were thawed in running cold water and inoculated in Columbia agar plates after the outer surface of the tube was disinfected with ethanol. The plates were incubated overnight (18 hours) at 37.degree. C. in an incubator with 6% CO.sub.2 atmosphere. The cultures were re-streaked on fresh plates to isolate pure cultures of *Neisseria meningitidis* and incubated at 37.degree. C. in 6% CO.sub.2 atmosphere overnight for 12 hours. Bacterial colonies from two plates were collected with a sterile cotton swab and suspended in two 10 ml aliquots of Shedulars Broth® (Remel, Inc.®) in separate 15 ml centrifuge tubes and re-suspended into 50 ml media contained in a 200 ml flask. The culture was allowed to grow in a shaker at 125 rpm, 35.degree. C. and normal atmospheric pressure for about 3 hours and then transferred into a 1 Liter flask containing 200 ml pre-warmed medium and again incubated at 125 rpm, 36.degree. C. for 12 hours to form a seed culture. An absorbance of 1.5 at 600 nm is considered equivalent to 500 Klett units. The culture was then transferred to a 2 Liter conical flask, containing 500 ml of the same medium, inoculated with 50 ml of the inoculum and incubated under the conditions previously described. Inoculum from eight flasks (the ratio of inoculum to the media is 1:10 or 8 L:80 L) were used to inoculate the bioreactor (New Brunswick® model MPP 80-total capacity 100 L) with 80 L of medium. The cultivation conditions were: temperature 35.0.degree. C.; air flow rate 5 L/min (0.125 vvm, superficial aeration); agitation frequency 120 rpm (with 2 Rushton six blade disc turbines); vessel head space pressure 6 psi; height and diameter of the vessel 72 and 40 cm, respectively; turbine diameter 16.5 cm, one located at 10 cm from the vessel bottom and the other at 35 cm. Four baffles were installed to enhance the mixture efficiency. The oxygen volumetric transfer coefficient (k.sub.La) was near 0.07 min.sup.-1 before the inoculation (t=0 h). The batch cultivations run under the same operational conditions, were divided into three groups, each one with three repetitions: the first one with Watson-Scherp medium, the second with Catlin medium; and the third with modified NMFM medium.

Analysis:

Cell concentration was articulated as dry biomass, as determined by centrifugation of a sample at 10,000.times.g, followed by drying the pellet at 60.degree. C. for 48 hrs. Polysaccharide concentration was assessed after bacterial cell removal and was precipitated by adding Cetavlon™ to the sample. The supernatant was removed after centrifugation and the precipitated biomass was re-suspended in a one Molar CaCl.sub.2.2H.sub.2O solution to obtain supernatant for polysaccharide determination using the following method: a sample containing 10-70 g of sialic acid is taken in a 16.times.150 mm glass tube with the sample volume brought up to 500 g/L. Standard solutions of sialic acid were prepared using 20, 40, 60, 80, and 100.mu.g, and each was made up to 500 g/L to which was added 50 micro-liters resorcinol reagent. The tubes were placed in boiling water bath for 15 min. If the tube shows blue/purple/brown color, it indicates that the sample contains sialic acid. Absence of blue color indicates that sialic acid is not present. A dark brown color indicates that the sample has either too high a concentration of sialic acid or that it is not pure enough. The tubes were cooled to room temperature (20-25.degree. C.) in cold water bath and 1 mL (2.times. sample volume) of extraction organic solvent was added into each test tube. The tubes were shaken vigorously and left at room temperature until the organic solvent layer separates completely from the aqueous phase. The top organic phase was transferred to a cuvette and the absorbance was determined against pure organic solvent in a spectrophotometer at 580 nm. Absorbance was compared with a standard curve for quantification, which detects the polysaccharide monomers (sialic acids) formed after acid hydrolysis. Yield coefficient was calculated by the ratio between polysaccharide production and cell biomass generated (Y.sub.P/X) for a given cultivation time. FIGS. 1-4 show the production associated with polysaccharides in the bacterial population up to the 20.sup.th hour of incubation.

The compositions of the culture media are:

Modified *Neisseria Meningitidis* Fastidious Medium (NMFM) for serogroups C, Y and W-135: (grams/Liter): Sodium chloride (NaCl), potassium phosphate dibasic (K2HPO4), ammonium chloride (NH4Cl), potassium sulphate (K2SO4), magnesium chloride ((MgCl2.6H2O), calcium chloride (CaCl2.2H2O), glucose, L-glutamic Acid, L-arginine, glycine, L-serine, L-cysteine.HCl, Fe (III) citrate, yeast extract (30 k dia-filtered) and antifoam dissolved in DI water.

Watson-Scherp Medium: grams/Liter: Sodium phosphate, dibasic 2.500; Soy peptone 5-30; Monosodium Glutamate 5.000; Potassium Chloride 0.103; Magnesium sulfate 0.732; L-Cysteine 0.016; Glucose 11.250

Catlin Medium (MCDA) Catlin, (in mM: NaCl, 100; KCl, 2.5; NH.sub.4Cl, 7.5; Na.sub.2HPO.sub.4, 7.5; KH.sub.2PO.sub.4, 1.25; Na3C6.H5.O7.2H2O, 2.2; MgSO.sub.4.7H.sub.2O, 2.5; MnSO.sub.4.H.sub.2O, 0.0075; L-glutamic acid, 8.0; L-arginine.HCl, 0.5; glycine, 2.0; L-serine, 0.2; L-cysteine HCl.H.sub.2O, 0.06; sodium lactate, 6.25 mg of 60% syrup/mL of medium; glycerin, 0.5% (v/v); washed purified agar, 1% (wt/vol) CaCl.sub.2.2H.sub.20, 0.25; Fe.sub.2(SO.sub.4).sub.3, 0.01)

Kinetics:

Kinetics of glucose consumption verses pH was evaluated for the various media. When the Watson-Scherp medium was used, 6 g/L of glucose consumption was observed at the end of the cultivation; with modified NMFM medium the residual concentration of the substrate was 3 g/L and with Catlin medium glucose consumption was between 5-6 g/L. The consumption of glucose during cultivation yielded acid metabolites in Watson-Scherp medium and Catlin medium. These results indicate that these media require adjustment of pH during the fermentation process. Modified NMFM medium does not require adjustment of the pH throughout cultivation of polysaccharide or vaccine production and provides minimal stress on the bacteria during the fermentation process. This fact indicating the absence of acid metabolites, also indicates that sequential consumption of amino acids (as a source of carbon) may have taken place.

The association between polysaccharide production and biomass is extremely important in endotoxin-free large-scale production. During cultivation of *N. meningitidis* serogroups A, C, Y, W-135 in a bioreactor it is crucial to pay attention to two criteria: attaining the maximum polysaccharide concentration at the end of the cultivation in the bioreactor ($P_f$) and simultaneously attaining the minimum cell debris (biomass) yield factor ($Y_{P/X}$) which is important for polysaccharide purification. The cell debris is nothing but endotoxin contaminant that must be removed in the purification process.

Statistical Analysis:

Statistical analysis was performed using test "t" at the 5% significance level to compare the data obtained from the three media used in this study. Greater final concentrations of polysaccharide (P) and greater cell/polysaccharide yield factors ($Y_{P/X}$) were obtained from group experiments 1 to 3, where the modified NMFM medium used resulted in an average of 45.25 mg/L. In addition, statistical tests on the biomass values determined at the end of the cultivations ($X_{max}$) showed that the use of Watson-Scherp medium resulted in production of a large biomass of $N$. $meningitidis$ and did not give best values for the yield factor ($Y_{P/X}$), compared to experiments carried out using the modified NMFM medium. This implies that there was a higher concentration of dry cellular biomass production when using Watson-Scherp medium and the lowest was found when using modified NMFM medium.

The results obtained from the experiments that used the modified NMFM medium with a glucose concentration of 10.0 g/L, showed that the residual glucose value at the end of the cultivation was lower than that obtained in Watson-Scherp medium and Catlin medium. Kinetics of nitrogen consumption by $N$. $meningitidis$ during polysaccharide production using the modified NMFM medium showed that adding the nitrogen source, in the presence of excess glucose, resulted in a greater production of polysaccharides. In 12 hours, the polysaccharide production using modified NMFM medium showed 45.25 mg/L at neutral pH, minimal dry mass of 0.32 g/L with lower utilization of carbon source compared to Watson-Scherp and Catlin media. The advantages of the modified NMFM medium are lower costs and easier cultivation and purification stages in the polysaccharide production process.

Procedure for the Production of Capsular Polysaccharide

Capsular polysaccharide production by *Neisseria meningitidis* serogroups A, C, Y, and W-135 was studied in batch experimental runs. The experiments were conducted in a set of 100 L bioreactors with 80% of modified NMFM cultivation medium. Cultivation temperature and pH were controlled at optimal pre-established values. The dynamic behavior of the bacteria was analyzed based on biomass growth, glucose uptake, polysaccharide production, and dissolved oxygen time profile obtained in a set of experimental runs with initial concentrations of glucose that varied from 5 to 13.5 g/L.

The preset set of controlled conditions for the production of polysaccharides maximized the accumulation of polysaccharides, low biomass, and endotoxin accumulation due to the lack of new bacterial cell formation. Although glucose was completely consumed, there was no significant difference in the final concentration of polysaccharides between the bioreactor runs using individual serotypes of *N. meningitidis*. Final concentrations of biomass were very similar among all serotypes for all experimental runs. The medium formulation of modified NMFM has limited phosphate availability, and resulted in lower biomass production, glucose consumption, endotoxin concentration, dissolved oxygen, better pH balance, and greater polysaccharide production for all *Neisseria meningitidis* serotypes. Thus, the designed preset conditions shall be employed for implementation of future process control and optimization of the industrial polysaccharide vaccine production with modified NMFM medium for Meningococcal meningitis serotypes A, C, Y, and W-135.

Concept for *Neisseria Meningitidis* Medium Invention:

Modified NMFM medium is more economical and cheaper than the previously invented NMFM medium (U.S. Pat. No. 7,491,517) which recites the same characteristics as follows:

NMFM medium is a highly-enriched bacteriological medium useful for growing fastidious bacteria. The bacterial cell growth in this medium is faster than in any other known synthetic and non-synthetic media. NMFM is useful for production of high quantities of toxin-free polysaccharide in a duration of less than or equal to 12 hours. Filter sterilized glucose and amino acids were added to the autoclaved cool medium, which improved production of polysaccharides by 25%. This type of process allowed non-degradation of heat sensitive sugars and amino acids and eliminated batch feeding during the fermentation process for polysaccharide production. Use of NMFM medium for Meningococcal meningitis vaccines saves almost 50% cut-off time in the fermentation process and purification of toxins, and results in clinically-proven safer vaccine production as compared to the use of Watson-Scherp and Catlin media, which require longer periods of fermentation and a more intensive toxin purification process. We used calcium carbonate ($CaCO_3$) to balance the pH of the medium, as opposed to the use of calcium chloride ($CaCl_2$), which can make media more alkaline during fermentation. Ionized calcium is the key buffer that helps to maintain the acid/alkaline balance in NMFM medium. We allowed the mutant strains of *Neisseria meningitidis* serotypes to grow slowly in a short period of incubation to reach lower maximal optical density and to produce more endotoxin-free polysaccharides (PS) than the use of standard media. Cox et. al., reported that the NMB1638 gene of *Neisseria meningitidis* was responsible for a lipopolysaccharide (LPS) containing lipid A that was characteristically phosphorylated with multiple phosphate and phosphoethanolamine residues. Mass spectroscopic analyses of the LPS of *Neisseria meningitidis* strains that had been inactivated by a specific mutation indicated that there were no phosphoethanolamine residues. *Neisseria meningitidis* produces two types of toxins called exotoxins and endotoxins. Exotoxins are released from bacterial cells and may act at tissue sites removed from the site of bacterial growth. Endotoxins are cell-associated substances that are structural components of the cell walls. However, endotoxins are released from growing bacterial cells or from cells which are lysed as a result of effective host defense. Hence, bacterial toxins, both soluble and cell-associated, may be transported by blood and lymph and cause adverse reactions in humans. Lipopolysaccharides are considered the major endotoxin in polysaccharide production. Removal of or minimal supplementation of organic phosphates in liquid cultures is very important in meningococcal polysaccharide production to reduce the production of endotoxins.

Gotschlich et. al, first reported effective method for purification of meningococcal polysaccharides from liquid cultures. Cationic reagent Cetavlon™ (hexadecyltrimethyl ammonium bromide) was used to precipitate anionic polysaccharides.

Inorganic phosphates ($P_i$) are required for any bacterium to function as constituents of nucleic acids, nucleotides, phospholipids, lipopolysaccharides (LPS) or toxins, and teichoic acids. In phosphate-deficient NMFM medium, the bacterium utilizes its intracellular phosphate reserve for its cellular function at minimum rates for production and release of undesirable LPS, or toxins, into the medium at minimal level. The NMFM medium does contain minimal inorganic phosphate (P.sub.i) salts, but is buffered by 10 mM morpholinepropanesulfonic acid (MOPS; pH 7.0). Due to the stress induced by pH balance combined with (P.sub.i) deficiency of the medium, NMFM medium allowed mutant strains of *Neisseria meningitidis* serotypes to grow more slowly, reach lower maximal optical densities, produce less toxins, and produce more polysaccharides (PS) than the standard media. *Neisseria meningitidis* serotypes synthesize capsular polysaccharides that are used as vaccine candidates. These molecules are produced by bacterium as a capsule under strong stressful conditions (both nutritional and physiological stress as stated above) and are tightly associated with the cell assembled as capsular polysaccharides (CPS) which surround the cell surface. When they are liberated into the medium they are called extracellular polysaccharides (EPS).

The capsule expressed by *N. meningitidis* is categorized as a group II capsule based on the similar chemical and physical properties of capsular polymers. Serogroup A is composed of (.alpha.1.fwdarw.6)-linked N-acetylmannosamine-1-phosphate. The capsules expressed by each of the other major invasive meningococcal serogroups Y and W-135 are composed of alternating units of D-glucose and D-galactose and sialic acid, respectively. The capsular polysaccharides of serogroups C are composed entirely of sialic acid in an (.alpha.2.fwdarw.8) or an (.alpha.2.fwdarw.9) linkage.

Phosphatase activity (P.sub.i) and pH balance induced increased polysaccharide production by *Neisseria meningitidis* isolates. Data are the average of the means of at least three independent experiments in which each experimental mean was derived from PS extracts of three separate cultures. Cells were incubated for 12 h in NMFM with (+) or without (−) phosphorus.

The tables below indicate the phosphatase activity of the respective serogroups shown below. (+) plus phosphates (+P.sub.i) in the tables below indicate, Thiamine pyrophosphate 0.10 g; K.sub.2HPO.sub.4 4.00 g, Na.sub.2HPO.sub.4 7.5. (−) minus phosphates (−P.sub.i) in the tables below indicate, Morpholinepropanesulfonicacid (MOPS; pH 7.0).

TABLE 1

| Serogroup A | | | | |
|---|---|---|---|---|
| PHOSPHATASE ACTIVITY | Culture Phosphate | | Assay pH | |
| mg-polysaccharides | +plus | −minus | 5.0 | 7.0 |
| 0 hours | 0 | 0 | 0 | 0 |
| 3 hours | 8 | 7.2 | 0.92 | 7.2 |
| 8 hours | 17 | 35 | 0.8 | 35 |
| 12 hours | 20 | 43 | 0.4 | 43 |

TABLE 2

| Serogroup C | | | | |
|---|---|---|---|---|
| PHOSPHATASE ACTIVITY | Culture Phosphate | | Assay pH | |
| mg-polysaccharides | +plus | −minus | 5.0 | 7.0 |
| 0 hours | 0 | 0 | 0 | 0 |
| 3 hours | 3 | 9 | 0.85 | 9 |
| 8 hours | 15 | 39 | 0.8 | 39 |
| 12 hours | 21 | 48 | 0.4 | 48 |

TABLE 3

| Serogroup Y | | | | |
|---|---|---|---|---|
| PHOSPHATASE ACTIVITY | Culture Phosphate | | Assay pH | |
| mg-polysaccharides | +plus | − minus | 5.0 | 7.0 |
| 0 hours | 0 | 0 | 0 | 0 |
| 3 hours | 2 | 8 | 0.5 | 8 |
| 8 hours | 3.7 | 25 | 0.2 | 25 |
| 12 hours | 8 | 43 | 0.13 | 43 |

TABLE 4

| Serogroup W-135 | | | | |
|---|---|---|---|---|
| PHOSPHATASE ACTIVITY | Culture Phosphate | | Assay pH | |
| mg-polysaccharides | +plus | −minus | 5.0 | 7.0 |
| 0 hours | 0 | 0 | 0 | 0 |
| 3 hours | 1.7 | 7.2 | 0.5 | 7.2 |
| 8 hours | 2.4 | 41 | 0.18 | 41 |
| 12 hours | 6 | 47 | 0.1 | 47 |

Preparation of Meningococcal Meningitis Polysaccharide Vaccine:

Proteins and nucleic acid contaminants were precipitated with ethanol followed by polysaccharide precipitation with Cetavlon™, a polycationic compound used specifically to collect polyanionic polysaccharides. The residual contaminants were further removed by proteinase digestion and ultrafiltration. In this invention, we also used the polycationic compounds to specifically collect polyanionic polysaccharides after precipitating with Cetavlon™ which gave high purity polysaccharide vaccine components. Overnight, CaCl.sub.2 was retained with Cetavlon™ precipitated polysaccharide at 4.degree. C. The polysaccharides were further precipitated by slow addition of ethanol to collect polysaccharide residues and to remove contaminants in the preparation to give absolute purification of the vaccine compound. The phenol extraction step as described in the prior art was replaced with activated carbon filtration. Activated carbon and Sephacryl gel filtration yielded high purity and quantity of polysaccharide vaccine components.

Polysaccharide Production in Modified NMFM Medium

The *Neisseria meningitidis* serotypes were grown in separate 100-L bioreactors in modified NMFM medium for eighteen to twenty hours (as described earlier). Absorbance unit: Optical Density (OD) of bacterial growth of 10 at 600 nm, after a fermentation process of 12 hours, was chosen for the cultivation of polysaccharides from *N. meningitidis*. Formaldehyde (36.5-38%) 1% (v/v) was added to the bioreactors at 25 psi to kill the bacteria and then centrifuged (5,000.times.g for 30 min) to remove bacterial cells. The supernatant was collected, treated with 100% ethanol by slow addition with agitation and centrifuged to collect the precipitate. The precipitate was re-dissolved in water and re-precipitated three times with ethanol by slowly adding 80% (v/v) ethanol, followed by centrifugation. The crude polymers were fractionated by stepwise precipitation with 1% hexa-decyl-tri-methyl-ammoniumbromide (Cetavlon™) at pH 7.0. at 4.degree. C. overnight.

The precipitate was collected by centrifugation and re-suspended in water and 10% Cetavlon to a final concentration of 0.1% (w/v) and an equal amount of 0.9 molar CaCl.sub.2 was then added to make a final concentration of 1 mM and the solution left overnight with continuous mixing or agitation at 4.degree. C. to remove endotoxin. The supernatant was collected by centrifuging at 9000 rpm. Cold ethanol was added to the supernatant to a final concentration of 25% and allowed to stand at 4.degree. C. for 2 hours. The supernatant was collected by centrifuging at 5000 rpm for 40 min. Low molecular mass residual contaminants were removed with proteinase K digestion and filtered through activated carbon to remove trace organic compounds, repeatedly until OD.sub.275 nm was <0.1. CPS was further purified by using the Sephacryl 200 gel filtration column using 50 mM ammonium formate elutions.

Meningococcal Oligosaccharide Linked Polysaccharides and Diphtheria Protein Conjugate Vaccine (PSOSDT)

In the preferred embodiment a method was developed for coupling carboxylic acid-containing oligosaccharides linked to activated polysaccharides and diphtheria protein for vaccine preparation. Oligosaccharides of Neisseria meningitidis serogroups A were isolated and the carboxylic acid at 2-keto-3-deoxyoctulosonic acid of the OS was linked through adipic acid dihydrazide to pre-activated polysaccharides and carrier protein as per Che-Hung Lee 2009. Where the carrier protein used in the present invention is diphtheria toxoid (DT).

The antigenicity of the OS linked diphtheria conjugated to polysaccharides was measured by enzyme-linked immunosorbent Assay (ELISA) and Serum Bactericidal Assay (SBA) using meningococcal vaccinated human antibodies. The OS-polysaccharide-protein conjugates derived from meningococcal vaccine may therefore be vaccine candidates to prevent meningitis caused by meningococci effectively, may be used for all ages and longer immunity against meningococcal infections caused by the serogroups A, C, Y and W-135 proved by human clinical trial.

Production of Polysaccharide-Oligosaccharide-Diphtheria Toxoid Conjugate Vaccine (PSOSDT)

The following method was used to link meningococcal oligosaccharides to polysaccharides and diphtheria protein to produce a conjugate vaccine for all ages.

The Production of Polysaccharide-Oligosaccharide-Diphtheria Toxoid Conjugate Vaccine (PSOSDT) has Five Major Steps:

Step 1: Isolation and purification of capsular polysaccharides from four meningococcal serogroups A, C, W-135 and Y Step 2: Derivatization of oligosaccharides (OS)

(A) Isolation of lipo-oligosaccharide from four meningococcal serogroups A, C, W-135 and Y (B) Removal of lipid A from Lipo-oligosaccharide to obtain oligosaccharides:

Step 3: Purification of Diphtheria toxoid (DT)

(A) Activation of Diphtheria toxoid (DT)

Step 4: All the three components PS, OS and DT were combined in a defined ratio for conjugation Step 5: Final formulation Step 1: Isolation and Purification of Capsular Polysaccharides from Four Meningococcal Serogroups A, C, W-135 and Y Isolation of polysaccharides from four meningococcal serogroups is done using culture supernatant-CTAB precipitation. Seed cultures were initially streaked on chocolate agar plate and incubated at 37° C. overnight in the presence of 5% $CO_2$. Grown culture is tested for its purity by gram staining, oxidase test and serogroup specific agglutination. Confirmed culture is streaked again on another chocolate agar plate for one more passage. Overnight healthy growth is transferred to 20 ml liquid broth and grown in a shaker incubator. 20 ml active growth is transferred to 180 ml broth in a 1 L flask. Active exponential growth of 200 ml culture is inoculated in 1.8 L broth in 4 L Erlenmeyer shake flasks. After reaching stationary state, culture is continued to incubate further 3-4 h. Later the shake flask culture is inactivated at 56° C. for 45 minutes. After bringing back to room temperature culture pellet is separated by centrifugation, and supernatant was given 0.1% CTAB and kept at 4° C. overnight. Crude polysaccharide precipitate is then separated by centrifugation. It is suspended in water and mixed with equal volume of 2M $CaCl_2$ to adjust to a final concentration of 1M $CaCl_2$ and allowed to mix for 2 h at room temperature. To this suspension was given 25% final concentration of ethanol to precipitate nucleic acids and proteins. Pellet is again separated by centrifugation. Supernatant was given final concentration of ethanol to 80%, mixed well and allowed to precipitate overnight at 4° C. Precipitated polysaccharide is further purified by nuclease enzyme followed by protease enzyme and dialyzed to remove nucleotides and peptides. Supernatant was given 0.1M $CaCl_2$ and subjected to ultracentrifugation to remove LOS. Ultra-supernatant was then dialyzed and concentrated to dryness. The polysaccharide is further purified by size exclusion and/or hydrophobic interaction column chromatographic methods. Purified polysaccharide is tested for any levels of contaminating nucleic acids, protein or endotoxin. Obtained vaccine grade polysaccharide structures were verified by $^1H$ NMR.

Step 2: Derivatization of Oligosaccharides (OS)

ADH (Aldrich Chemical Co., Milwaukee, Wis.) was coupled to oligosaccharides by carbodiimide-mediated condensation with 1-ethyl-3-(3-dimethylaminopropyl) carbodiimide (EDC) and N-hydroxysulfosuccinimide (sulfo-NHS) (Pierce) as per (51)

Isolation of Lipo-Oligosaccharide from Four Meningococcal Serogroups A, C, W-135 and Y:

Lipo-oligosaccharide from individual serogroup is isolated from culture pellet with hot phenol-water method. Water layer and phenolic layer after extraction were separately processed for LOS yields. Both layers were extensively dialyzed against tap water and later against DI water. Dialyzed material was concentrated by lyophilization to dryness. Concentrated material was run by sephadex G-150 size exclusion column and fractions were analyzed for neutral sugar. Sugar positive material was pooled and concentrated according to expected sizes. Later samples were run DOC-PAGE gels to stain the LOS by periodate-silver nitrate staining method. LOS was transferred to PVDF membrane and western were run to see the identity of individual serogroups.

Removal of Lipid a from Lipo-Oligosaccharide to Obtain Oligosaccharides:

Purified LOS is treated with 1% acetic acid at 90° C. for 2 h for breaking the ketosidic linkage between oligosaccharide and lipid A. After the hydrolysis the mixture is extracted with chloroform:methanol (2:1) to separate lipid A into organic layer. Aqueous layer is dialyzed and concentrated. Sugar content is estimated. Oligosaccharide is estimated by NMR and sugar analysis to confirm the serogroup specific saccharide.

Step 3: Purification of Diphtheria Toxoid (DT)

Diphtheria toxoid was concentrated and passed through a Sephacryl S-300 column equilibrated with 0.9% NaCl containing 0.02% sodium azide. The protein concentration was measured by the micro-bicinchoninic acid method (Pierce, Rockford, Ill.) (50), and bovine serum albumin (BSA) was used as a standard.

Activation of Diphtheria Toxoid (DT):

Activation of DT to contain hydrazide groups (DT, 4.0 mg/mL) was activated with 0.40M hydrazine in the presence of 20 mM EDC, 0.1M 2-morpholinoethanesulfonic acid (MES), pH 6.5 at 20-24° C. (Lee et al). The protein concentration of the resulting DT-hydrazide (DTH) sample was determined by Lowry assay or BCA assay using BSA as reference. The hydrazide content was determined by TNBS assay using ADH as reference. The degree of activation (DA, number of hydrazide per DT molecule) was calculated from the molar concentrations of hydrazide and DT assuming 150,000 kDa for the molecular weight of DT which is similar results published by Lee et. Al.

Step 4: all the Three Components PS, OS and DT were Combined in a Defined Ratio for Conjugation Obtained purified PS and OS were considered at predetermined ratios. They are separately activated with sodium periodate. PS was size reduced to suitable levels before considered for activation by 0.1% acid hydrolysis in case of A, W135 and Y. Group C is not considered for size reduction as C polysaccharides can be size reduced during periodate activation.

Diphtheria toxoid is activated by hydrazine to create hydrazide groups on the protein. Serogroup specific activated PS and activated OS are combined at a predetermined ratio with activated DT to conjugate. After establishing covalent linkage, unused active aldehyde groups were capped using sodium borohydride reduction. Unconjugated DT, PS and OS are removed by size exclusion chromatography. Finally in this conjugation we end-up creating three populations a) PS-DT-OS b) PS-DT c) OS-DT at 4:3:0.5 ratio.

Step 5: Final Formulation

The above procedure arrived at an aseptically formulated concentration where the vaccine formulation will finally have doses in the ratio of 8:8:1 (PS:DT:OS) based on polysaccharide and DT contents. For example, each dose contained: (A) 4 ug PS:4 ug DT:0.5 ug OS, (B) 2 ug PS:2 ugDT:0.25 ug OS.

Results

Animal Pharmacology and Toxicology Studies

Animal studies conducted at Spring Valley Laboratories, Woodbine, Md., USA, under the guidance from JN International, Inc, USA involving 24 Balb/c mice and 24 Neonatal mice have demonstrated that NmVac A, C, Y & W-135 DT conjugate is safe and non-toxic. In-vitro bactericidal assays conducted at Central Research Institute, Nebraska has demonstrated that NmVac A, C, Y & W-135 DT conjugate elicited good immune response providing sero-conversion rates as measured by bactericidal antibody assays: Sensitivity: Group A: 81%, Group C: 87%, Group Y: 90% and Group W-135: 82%; Specificity: Group A: 86%, Group C: 82%, Group Y: 91% and Group W-135: 93%.

It can be easily understood by persons of ordinary skill in the art that the modified NMFM Medium (*Neisseria Meningitidis* Fastidious Medium) can have several other possible combinations of the ingredients of the medium and the embodiment of the modified NMFM medium described herein is limited only by the claims made herein.

Human Clinical Trials

Clinical trials were conducted to evaluate the immunogenicity, protective efficacy and safety of the vaccine NmVac A, C, Y & W-135 DT conjugate vaccine, against meningococcal infection, compared to Aventis Pasture Menactra A, C, Y and W-135 DT conjugate vaccine.

The two assay techniques used in the study were ELISA to detect anti meningococcal antibodies and serum bactericidal assay (the prevalence of meningococcal disease is inversely proportional to the polysaccharide specific bactericidal titre in the serum)

ELISA

Noncompetitive ELISAs used to detect anti meningococcal antibodies involve: 1) coating of a microtiter plate with the antigen to be studied; 2) blocking of unbound sites on the plate with an immunologically neutral protein; 3) addition of test sera and specific binding of antibodies to the solid-phase antigen on the plate; 4) addition of a detector antibody that recognizes the class or subclass of serum antibody; 5) generation of a color change on the ELISA plate linked to the amount of bound detector antibody; 6) calculation of concentration of specific antibodies in test sample.

Principle of Serum Bactericidal Assay

*N. Meningitidis* target strains are lysed in the presence of meningococcal specific antibody and complement (antibody mediated complement dependent killing). Serial dilutions of human sera are incubated with appropriate target strains and complement. Meningococcal specific antibody binds to the target cell surface via meningococcal specific protein or carbohydrate moieties. The serum bactericidal titer for each unknown serum is expressed as the reciprocal serum dilution yielding 50% killing as compared to the number of target cells present before incubation with serum and complement.

Study Design

The study was a double blinded randomized controlled single arm experiment in Africa to evaluate the safety, protective efficacy and immunogenicity of quadrivalent meningococcal meningitis vaccine (NmVac A, C, Y & W-135 DT conjugate vaccine) in healthy subjects using an established product in the market Menactra A, C, Y and W-135 DT conjugate as a control.

Vaccine Administration and Sampling

The trial was conducted on 101 volunteers between the ages of 13-30 years of both genders fulfilling the eligibility criteria in city of Bouake in Ivory Coast. The Participants were coded, randomized and given a single dose of the coded vaccine. Both vaccines were administered intramuscularly in the deltoid region of the arm.

NmVac A, C, Y, W-135 DT conjugate vaccine is a sterile, clear to slightly turbid liquid, composed of *Neisseria Meningitidis* serogroups A, C, Y and W-135, purified capsular polysaccharides antigens, each of them conjugated to diphtheria toxoid protein. Each 0.5 ml dose of the vaccine is formulated in sodium phosphate buffered isotonic sodium chloride solution to contain 4 μg each of meningococcal A, C, Y and W-135 polysaccharides conjugated to approximately 48 μg of diphtheria toxoid protein as a carrier. It also contains Lactose as a stabilizer.

Blood samples were obtained 2 weeks pre-vaccination, 2 weeks and 8 weeks post-vaccination. Antibody response was determined using Serum Bactericidal Antibody assay. All the samples were reported at Pasteur Institute, Ivory Coast. Serum Bactericidal Antibody titres of 128 and above were taken to be protective and of positive seroconversion.

Results

The clinical study conducted to evaluate the immunogenicity, protective efficacy and safety of a new vaccine NmVac A, C, Y and W-135 DT conjugate against meningococcal infection, in volunteers 13-30 years of age, both male and female, in the city of Bouake in Ivory Coast, compared to Aventis Pasture Menactra A, C, Y and W-135 DT conjugate vaccine, presently in the market showed the following results.

The primary objective was to evaluate the immunogenic response to NmVac A, C, Y and W-135 DT conjugate vaccine, compared to Aventis Pasture Menactra A, C, Y and W-135 DT conjugate vaccine. This was done by estimating the Serum Bactericidal Antibody Titres at 2 and 8 weeks post-vaccination. Titres above 128 were taken to be positive for seroconversion and protective efficacy.

The primary hypothesis to show that NmVac A, C, Y and W-135 DT conjugate vaccine, is non inferior to Aventis Pasture Menactra A, C, Y and W-135 DT conjugate vaccine was achieved for serogroup A. The upper limit of the one-sided 95% confidence interval of the difference of the proportion of subjects achieving seroconversion for the two vaccine groups is less than 0.10. The upper limit of the two-sided 95% confidence interval is also evaluated and found to be less than 0.1 in accordance with the current preferences of the United States Center for Biologics Evaluation and Research (CBER) for testing non-inferiority immunogenicity hypotheses. For the other Serogroups C, Y, and W-135, the upper limit of the one-sided 95% confidence interval of the difference of the proportion of subjects achieving seroconversion for the two vaccine groups is slightly above 0.1.

The secondary objective was to evaluate the safety of the NmVac A, C, Y and W-135 DT conjugate vaccine, compared to Menactra A, C, Y and W-135 DT conjugate vaccine in the population of City of Bouake. This was done by monitoring for immediate reactions 15 minutes post-vaccination and the local and systemic reactions were noted in the case report form before discharge. Further the participants were contacted by the medical officer at 24 hours, 48 hours and 72 hours for pre-specified adverse events which included local reactions (pain, erythema, swelling and induration) and systemic reactions (fever, rash, headache, photophobia, weakness, myalgia, arthralgia, nausea, vomiting, abdominal pain, diarrhea). Adverse events were also monitored at the subsequent Visits at week 2 and week 8. There were no immediate reactions or serious adverse events in participants of both vaccine groups.

The overall local reactions were fewer in the NmVac A, C, Y and W-135 DT conjugate vaccine recipients, compared to Menactra A, C, Y and W-135 DT conjugate vaccine recipients. The most common local reaction was pain at the vaccine administration site, followed by swelling/induration. No systemic reactions were reported in the NmVac A, C, Y and W-135 DT conjugate vaccine recipients, whereas in the Menactra A, C, Y and W-135 DT conjugate vaccine recipients the most common systemic adverse reaction was headache (3.85%), followed by nausea (1.92%).

The phase III clinical trial report details that the NmVac A, C, Y and W-135 DT conjugate vaccine is non inferior to Menactra A, C, Y and W-135 DT conjugate vaccine with regards to safety of the vaccine, also the study demonstrates a better safety profile for the new vaccine. The immunogenicity of the vaccine is non inferior to Menactra partially at 8 weeks.

The invention claimed is:

1. A modified *Neisseria meningitidis* fastidious culture medium (NMFM) for producing a higher amount of capsular polysaccharides and a lesser amount of cellular biomass from *Neisseria meningitidis* comprising: DI (deionized) water, NaCl, $K_2HPO_4$, $NH_4Cl$, $K_2SO_4$, $MgCl_2.6H_2O$, $CaCl_2.2H_2O$, Glucose, L-Glutamic Acid, L-Arginine, Glycine, L-Serine, L-Cysteine.HCl, Fe (111) Citrate, Yeast Extract (30 k dia-filtered), and antifoam, with the pH of the composition maintained from 6.5 to 7.0 for serogroups A, C, Y and W-135 and characterized in that the use of the medium yields a higher percentage of polysaccharides and a lower percentage of cellular biomass as compared to Catlin or Watson-Scherp medium.

2. The culture medium according to claim 1, a liter comprising: 800 mL of DI (deionized) water, NaCl—5.60 g, $K_2HPO_4$—4.10 g, $NH_4Cl$—1.00 g, $K_2SO_4$—0.90 g, $MgCl_2$-$6H_2O$—0.35 g, $CaCl_2.2H_2O$—0.03 g, Glucose—10.0 g, L-Glutamic Acid—3.80 g, L-Arginine—0.10 g, Glycine—0.20 g, L-Serine—0.50 g, L-Cysteine-HCl—0.10 g, Fe (111) Citrate—0.04 g, Yeast Extract (30 k dia-filtered)—0.1%, and antifoam-0.1 ml, with the pH of the composition maintained from 6.5 to 7.0 for serogroups A, C, Y and W-135, where the medium yields a higher percentage of polysaccharides and a lower percentage of cellular biomass as compared to Catlin or Watson-Scherp medium.

* * * * *